(12) United States Patent
Li et al.

(10) Patent No.: US 7,907,275 B2
(45) Date of Patent: Mar. 15, 2011

(54) TYPE SELECTIVE AND POLARIZATION SELECTIVE DEVICE FOR RAMAN SPECTROSCOPY

(75) Inventors: Jingjing Li, Palo Alto, CA (US);
Zhiyong Li, Redwood City, CA (US);
Wei Wu, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 116 days.

(21) Appl. No.: 12/488,318

(22) Filed: Jun. 19, 2009

(65) Prior Publication Data

US 2010/0321685 A1    Dec. 23, 2010

(51) Int. Cl.
*G01J 3/44* (2006.01)
(52) U.S. Cl. ........................................................ 356/301
(58) Field of Classification Search ................ 356/301
See application file for complete search history.

(56) References Cited

U.S. PATENT DOCUMENTS

| | | | | |
|---|---|---|---|---|
| 7,713,849 | B2 * | 5/2010 | Habib et al. ................... | 438/479 |
| 7,733,481 | B1 * | 6/2010 | Bratkovski et al. ........... | 356/301 |
| 2006/0038990 | A1 * | 2/2006 | Habib et al. ................... | 356/301 |
| 2007/0058686 | A1 | 3/2007 | Capasso et al. | |

OTHER PUBLICATIONS

Muhlschlegel, et al. "Resonant Optical Antennas", Science, vol. 308, Jun. 10, 2005, pp. 1607-1609.
Crozier et al. "Surface Plasmons/Optical Antennas", http://www.seas.harvard.edu/crozier/research2.html (accessed via web Mar. 30, 2009),chosen for Applied Phys. Ltrs. cover, Oct. 2007.

* cited by examiner

*Primary Examiner* — Tarifur R. Chowdhury
*Assistant Examiner* — Isiaka O Akanbi

(57) ABSTRACT

A type and polarization selective device for Raman spectroscopy includes a set of at least two antennas and a gap at their intersection. First antenna geometry is such that it is configured to resonate, for first or second (different from the first) polarization, at a predetermined stimulation frequency of a material for which Raman scattering is to be studied, or at a Stokes or anti-Stokes frequency corresponding with the material when excited at stimulation frequency. Second antenna geometry is such that it is configured to resonate, for the other of second or first polarization, at the Stokes frequency when the first antenna is configured to resonate at the stimulation or anti-Stokes frequency, or at the anti-Stokes frequency when the first antenna is configured to resonate at the stimulation or Stokes frequency, or at the stimulation frequency when the first antenna is configured to resonate at the Stokes or anti-Stokes frequency.

20 Claims, 5 Drawing Sheets

TYPE SELECTIVE AND POLARIZATION SELECTIVE DEVICE FOR RAMAN SPECTROSCOPY

STATEMENT OF GOVERNMENT INTEREST

This invention has been made with Government support under Contract No. HR0011-09-3-0001, awarded by the Defense Advanced Research Projects Agency. The government has certain rights in the invention.

BACKGROUND

The present disclosure relates generally to type selective and polarization selective device(s) for Raman spectroscopy.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (virtual) energy state by the local electromagnetic field, which is ordinarily in the optical frequency domain. The excited molecule then radiates as a dipole source under the influence of the environment in which it sits at a frequency that may be relatively low (i.e., Stokes scattering), or that may be relatively high (i.e., anti-Stokes scattering) compared to the excitation signal. In some instances, the Raman spectrum of a given material shows multiple pairs of Stokes/anti-Stokes peaks. For each pair, the frequency difference between the excitation signal and the Stokes signal is the same as that between the anti-Stokes signal and the excitation signal. While Raman scattering is very useful, the magnitude of Raman scattering is typically very low. Furthermore, the polarization of the Raman signal is ordinarily random unless otherwise influenced by the environment.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Optical antennas have been used to enhance Raman scattering. Such optical antennas are often made from plasmonic materials (e.g., noble metals such as gold and silver). When properly designed, the electric field in a certain small area (i.e., the hot spot) around the antenna is much stronger than that of the incident electromagnetic (EM) wave in a certain frequency range around the resonant frequency of the antenna. An optical antenna ordinarily responds to the incident optical wave with a certain polarization, and the polarization of this optical antenna is defined as the polarization of this optical wave. When a material of interest (or an object made of the material of interest) is placed at the hot spot, the Raman scattering of this material is greatly enhanced in either the excitation process or the radiation process, or both. Optical antennas may be configured to enhance the local field that stimulates the Raman process.

Still further, the existence of the optical antenna can enhance the radiation of the Raman signal. The enhancement of the radiation can be equivalently described by the local field enhancement of the antenna under an incident EM wave at the Raman radiation frequency. If both the stimulating frequency and the Raman scattering frequency (Stokes and/or anti-Stokes) are close to the resonant frequency of the antenna, one single optical antenna is capable of enhancing the Raman scattering in both processes. However, the Raman shift (i.e., the difference between the frequency of the Raman signal and the stimulating EM wave) is often large, and, in some instances, is much larger than the bandwidth of the optical antenna. The present inventors have found that, in such instances, the optical antenna enhances the Raman scattering in either, but not both, the stimulating process or the radiation process when the optical antenna resonant frequency is properly designed. It is to be understood that in the various embodiments discussed herein, the Stokes or the anti-Stokes frequency refers to that of the first characteristic Stokes anti-Stokes pair that is the closest to the excitation/ stimulation frequency of the material, unless specified otherwise. In the embodiments disclosed herein, each antenna of the multi-antenna devices are specifically configured/designed so that the respective resonant spectrums cover one of the stimulating frequency, the Stokes frequency or the anti-Stokes frequency.

Figure 1A:
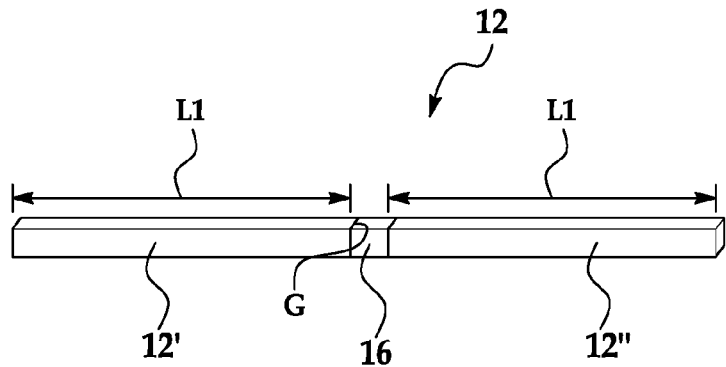
FIG. 1A is a perspective view of a linear antenna including two segments and a material-filled gap therebetween.

FIG. 1A illustrates an optical antenna 12 that is linear (i.e., it extends in a single direction, with no curve or bend). The antenna 12 includes two wire segments 12', 12", each of which is made of plasmonic materials. The wire segments 12', 12" have a gap G therebetween. The polarization of such a linear optical antenna 12 is along the direction of the wire segments 12', 12". The field at and around the gap G is greatly enhanced when operating at or around the resonant frequency of the antenna 12. When the material or object 16 for the Raman scattering is placed at the gap G, the Raman scattering can be enhanced due to the effects previously described.

Figure 1B:
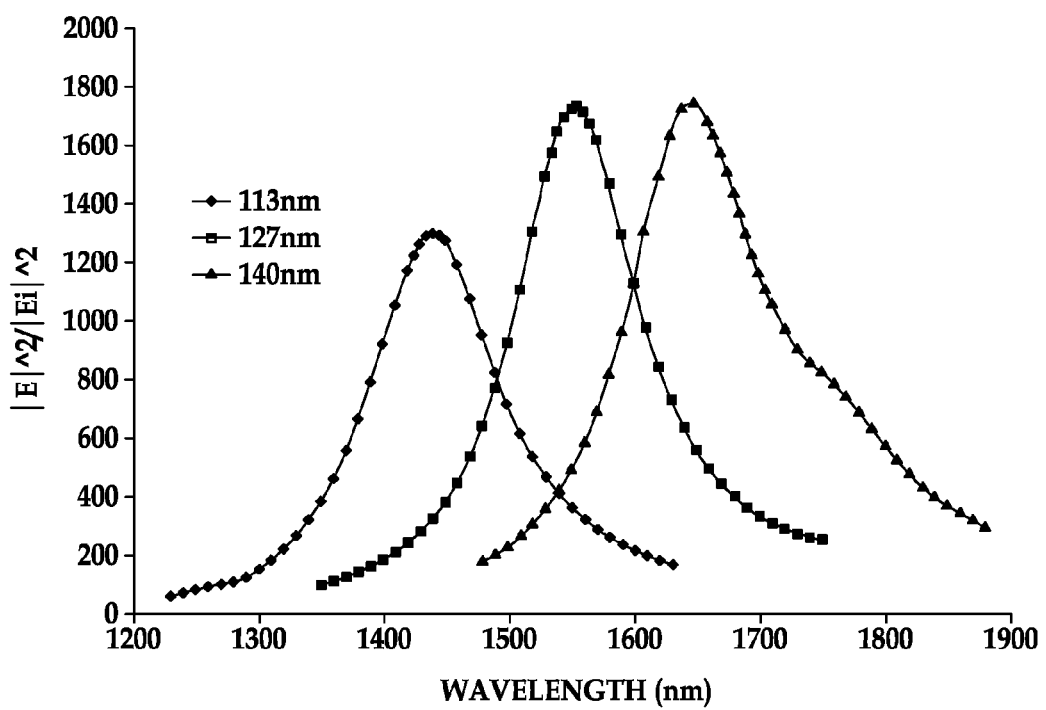
FIG. 1B is a graph illustrating, for three different linear antennas, the ratio of the square of the electric field magnitude at a center of a respective one of the linear antennas to the square of the incident wave as a function of wavelength.

The present inventors have found that the resonant frequency depends, at least in part, on the geometry of the antenna 12 and the properties of the material 16 used in the gap G of the antenna 12. Three different antennas having shapes similar to that shown in FIG. 1A were studied numerically to generate this conclusion. Specifically, these antennas each had a width of 20 nm and a 20 nm by 20 nm gap. FIG. 1B illustrates the ratio of the square of the electric field magnitude at the center of each of the three different antennas to that of the incident wave as the frequency changes. The half length L1 of the antenna 12 (i.e., the length L1 of each segment 12', 12" of the antenna 12) was different for each antenna, as indicated in the key of the graph. The frequency response curve changes greatly when the antenna geometry configuration is changed.

The Stokes and/or anti-Stokes frequency for which an antenna 12 is configured depends, at least in part, on the material selected and the excitation/stimulation frequency selected (which e.g., as shown in FIG. 1B, is used to determine the geometry of the antenna 12). This is due, at least in part, to the fact that for a given material, the frequency difference between the stimulation frequency and the Stokes/anti-Stokes signal is fixed. As such, when a particular material is excited at different frequencies, the Stokes and anti-Stokes frequencies are different. For example, if a particular material is excited at 1000 nm, the Stokes frequency may be 1005 nm while the anti-Stokes frequency may be 995 nm, but if the particular material is excited at 2000 nm, the Stokes frequency may be 2020 nm while the anti-Stokes frequency may be 1980 nm. Thus, the Stokes and/or anti-Stokes frequencies for which the antennas 12 disclosed herein are configured depend upon the excitation/stimulation frequency.

Embodiments of the device disclosed herein include one or more antenna sets 10, each set 10 including two or more optical antennas 12, 14 (see, e.g., FIG. 2) that share a gap G at their intersection, as described further hereinbelow. When the device is to be used, the material 16 to be studied is placed in the gap G, where the local electromagnetic field is enhanced by one or more the antennas 12, 14 of the device. The optical antennas 12, 14 are linearly polarized with polarizations that are different from each other, and are designed to resonate at different frequencies (i.e., each corresponds to the stimulation frequency, the Stokes Raman scattering frequency or the anti-Stokes Raman scattering frequency). As such, each optical antenna 12, 14 in a particular set 10 of the embodiments disclosed herein is type selective (i.e., may be configured to resonate at the stimulating frequency, the Stokes Raman scattering frequency, or the anti-Stokes Raman scattering frequency) and is also polarization selective. In some embodiments, the device is capable of selectively enhancing the Stokes or the anti-Stokes Raman signal, and the Raman signal is at a specified polarization different from that of the stimulating electromagnetic wave. In other embodiments, the Stokes and the anti-Stokes Raman scattering are both enhanced, but are radiated with different polarizations.

Figure 2:
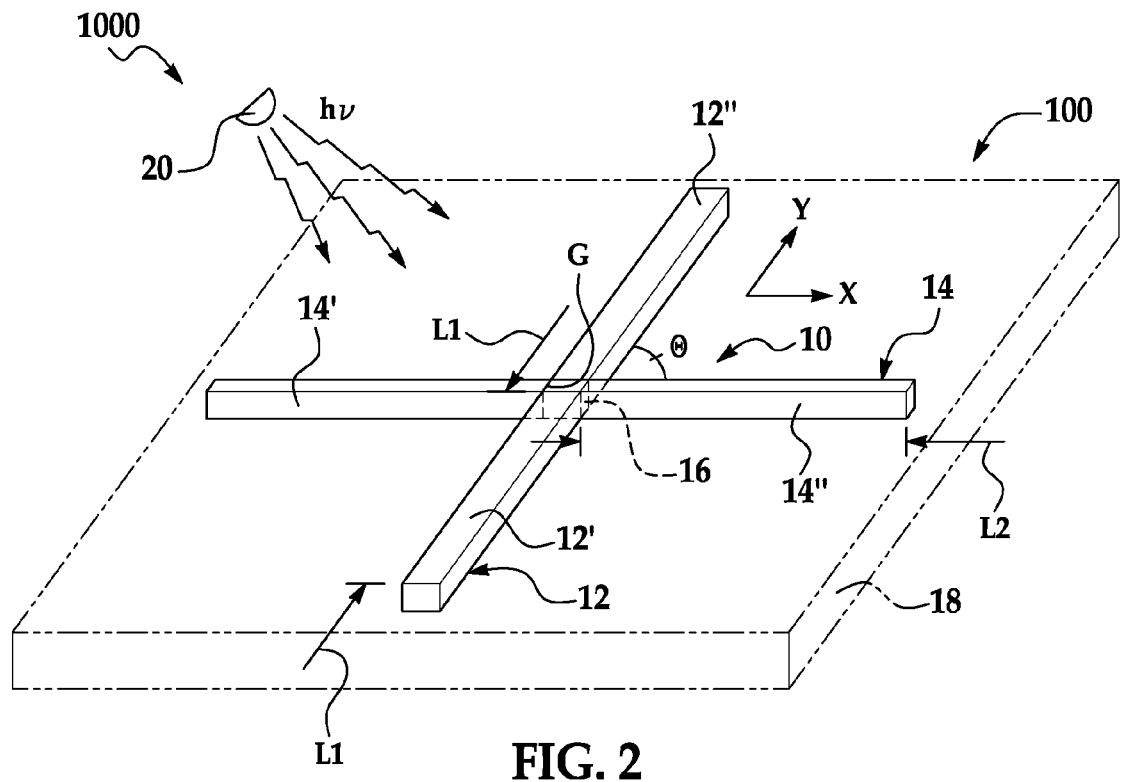
FIG. 2 is a perspective view an embodiment, in accordance with the present disclosure, of a system and a device including a single antenna set for type selective and polarization selective Raman spectroscopy.

Referring now to FIG. 2, an embodiment of the device 100 for type selective and polarization selective Raman spectroscopy is depicted. This embodiment of the device 100 includes one antenna set 10 having two antennas 12, 14. The antennas 12, 14 are linear (i.e., extend in a single direction, with no curve or bend). It is to be understood that other antenna geometries may also be used. Non-limiting examples of such other geometries are bow-tie antennas and elliptic, spherical, or faceted nanoparticle dimer antennas. As shown in FIG. 2, the antennas 12, 14 are positioned such that they cross each other at some non-zero (and non-180°) angle θ. In one embodiment, θ equals 90°, such that the two antennas 12, 14 are perpendicular to each other. As mentioned briefly hereinabove, the area at which the antennas 12, 14 intersect is a gap G where neither of the antenna 12, 14 material is present. In one embodiment, the gap G is empty after antenna 12, 14 fabrication so that the desirable Raman sample of interest may be introduced therein. In another embodiment, the gap G is filled with any desirable material 16 to be studied via Raman spectroscopy during antenna fabrication 12, 14.

The characteristics of the antennas 12, 14 (including the lengths (shown as L1 and L2 in FIG. 2) of the respective antenna segments 12', 12" and 14', 14") and direction (e.g., X, Y, etc.)) and of the gap G (including the size) will depend, at least in part, upon the desirable operation of the device 100. The desirable operation of the device 100 will depend, at least in part, upon the material 16 to be studied using the antenna set 10. As such, gap G and antennas 12, 14 are selected to generate a set 10 that functions in a predetermined manner for the material 16 of interest. More specifically, the characteristics selected will enable one to configure the device 100 with set(s) 10 having antennas 12, 14 that resonate at desirable frequencies and have stimulation signal enhancement or scattering enhancement in desirable, different polarizations.

As mentioned hereinabove, the material 16 to be introduced into the gap G is selected because its Raman scattering is of interest. The existence of the material 16 in the gap G influences the frequency property of one or both of the antennas 12, 14. Knowing the material 16 to be introduced into the gap G enables one to design each antenna 12, 14 to resonate at the specified stimulating frequency, the Stokes frequency of the selected material 16, or the anti-Stokes frequency of the selected material 16 when the material 16 is placed in the gap 16. It is to be understood that when a material 16 exhibits multiple peaks at different frequencies, one or more of the antennas 12, 14 may be configured to resonate at the Stokes or anti-Stokes frequency of that particular peak (this is described further hereinbelow in reference to FIGS. 4 and 5). As such, the material 16 of interest is selected, the antennas 12, 14 are designed and manufactured to resonate at the desirable respective frequency, and then the material 16 is placed in the gap 16.

When the design of the antenna set 10 corresponds with the resonance of two or more different materials 16 of interest, it is to be understood that upon manufacturing such an antenna set 10, the gap G may be left empty. Such an antenna set 10 may be incorporated into a device 100 including an array of different antenna sets, where each antenna set 10 in the array is configured to detect a different frequency peak of one of the two or more particular materials 16 of interest. The array enables such a versatile antenna set 10 to be used to study one particular material 16. It is to be understood that the material 16 of interest may be added to each antenna 10 in the array when it is desirable to study the material 16.

The material 16 may be a particle made of the desirable material, or may be a particle-like single object, such as a molecule. Non-limiting examples of gap G materials 16 include silicon, silicon nitride, and polymers. Other non-limiting examples of materials 16 (e.g., in the form of particles or particle-like objects) include quantum dots made up of a dielectric material, quantum dots made up of a semiconductor material, chemical species, biological species (e.g., virus, cells, toxins, disease marker molecules, or the like), other organic molecules, or combinations thereof. Some other non-limiting examples of suitable materials 16 include explosive molecules (e.g., TNT, plastic explosives, etc.), or hazardous molecules (e.g., VOC (volatile organic compounds), $CO_2$, CO, and toxic gases, such as phosphine nitroxide gases, etc). Suitable materials 16 may include any molecules of environmental, health, and/or security interest.

The size of the gap G is generally small in order to achieve a large field enhancement. The size of the sides of the gap G will depend, at least in part, on the width of each of the antennas 12, 14, and the depth of the gap G will depend, at least in part, on the height of each of the antennas 12, 14. In one non-limiting example, the gap G is 20 nm by 20 nm in size, and has a depth of the thickness (i.e., height) of the antenna 12, 14.

Each of the optical antennas 12, 14 is configured to respond to an incident optical wave with a predetermined polarization. The polarization of a linear optical antenna 12, 14 is along the direction of the particular antenna 12, 14. For example, and as shown in FIG. 2, the polarization of the antenna 12 is in the Y direction while the polarization of the antenna 14 is in the X direction. In this example, the polarizations are perpendicular to each other. When the incident wave has the same polarization as that of one of the antennas 12, 14, the local field will be greatly enhanced at the resonant frequency of that particular antenna 12, 14. As such, the respective antennas 12, 14 can be used to either enhance the stimulating process or the radiation process in the Raman scattering. It is to be understood that a respective antenna 12, 14 does not enhance both stimulation and radiation, because the resonant spectrum of each antenna 12, 14 is deliberately designed to cover a different frequency than that of the other antenna 14, 12. In some of the embodiments disclosed herein, excitation signals of one polarization at the stimulating frequency may be used to stimulate the device 100 via the assistance of one of the antennas 12, 14 having the same polarization, and Raman signals at the Raman-shifted radiation frequency and of another polarization will be transmitted from the device 100 (and in some instances detected) with the assistance of the other antenna 14, 12, which is a radiation-enhancing antenna corresponding with the other polarization.

Adjusting the respective half-lengths L1, L2 of the antennas 12, 14 (also referred to herein as the lengths L1, L2 of the respective antenna segments 12', 12" and 14', 14", where each segment 12' and 12" or 14 and 14" in an antenna 12 or 14 is equal to the other segment 12" and 12' or 14" and 14' in the antenna 12 or 14) enables the antennas 12, 14 to be individually tuned to a particular resonating frequency. In the embodiments disclosed herein, since it is desirable that the antennas 12, 14 resonate at different frequencies, the length L1, of the segments 12', 12" will, in some embodiments, be different from the length L2 of the segments 14', 14". For antennas 12, 14 having a shape other than linear shape shown in the Figures, the resonant frequency can, in principle, be adjusted by varying the geometry shape of the antennas 12, 14. For example, it is believed that the frequency of a linear antenna 12, 14 will be different from the frequency of a bowtie-shaped antenna (not shown).

Non-limiting examples of materials for each of the antennas 12, 14 include plasmonic materials, such as any noble metal (e.g., gold, silver, etc.), copper, aluminum, or any alloys thereof. Furthermore, the first and second antenna 12, 14 may be formed of the same metal, or of different metals. Selecting different metals for the respective antennas 12, 14 will contribute, at least in part, to the antennas 12, 14 giving off different resonances.

As non-limiting examples, the following devices 100 may be achieved by selecting a material 16 of interest to be studied, and then selecting appropriate antenna 12, 14 and gap G dimensions to achieve desirable resonating frequencies at desirable peaks of the material 16 and polarizations for the material 16. It is to be understood that FIG. 2 will be used to explain the various configurations of the device 100 in the following three paragraphs.

In one embodiment, the device 100 includes one antenna 12 (referred to in this example as the stimulating-enhancing antenna) that resonates at the stimulation frequency of the material 16, while the other antenna 14 (referred to in this example as the radiation-enhancing antenna) resonates at the related Stokes frequency of the material 16. In this example, the antenna 12 has Y polarization, and the antenna 14 has X polarization. In this example, the incident wave is selected to have Y polarization (i.e., the same polarization as the stimulating-enhancing antenna 12). When exposed to the incident wave, the stimulating-enhancing antenna 12 enhances the local electromagnetic field at the gap G so that the Raman scattering probability is increased due to the enhancement in the stimulation process. The radiation process of the Raman scattering is then further enhanced due to the existence of the radiation-enhancing antenna 14, and, in this example, the radiated Raman signals are predominantly of the Stokes type. Further, the polarization of the Raman signal is predominantly that of the radiation-enhancing antenna 14, which, in this non-limiting example, is X polarization.

In another embodiment, the device 100 includes one antenna 12 (referred to in this example as the stimulating-enhancing antenna) that resonates at the stimulation frequency of the material 16, while the other antenna 14 (referred to in this example as the radiation-enhancing antenna) resonates at the related anti-Stokes frequency of the material 16. In this example, the antenna 12 has Y polarization, and the antenna 14 has X polarization. In this example, the incident wave is selected to have Y polarization (i.e., the same polarization as the stimulating-enhancing antenna 12). When exposed to the incident wave, the stimulating-enhancing antenna 12 enhances the local electromagnetic field at the gap G so that the Raman scattering probability is increased due to the enhancement in the stimulation process. The radiation process of the Raman scattering is then further enhanced due to the existence of the radiation-enhancing antenna 14, and, in this example, the radiated Raman signals are predominantly of the anti-Stokes type. Further, the polarization of the Raman signal is again predominantly that of the radiation-enhancing antenna 14, which, in this non-limiting example, is X polarization.

In still another embodiment, the device 100 includes one antenna 12 that resonates at the related Stokes frequency of the material 16, while the other antenna 14 resonates at the related anti-Stokes frequency of the material 16. In this example, both antennas 12, 14 are configured to be used as radiation-enhancing antennas; however, one (i.e., antenna 12) is positioned in the Y direction and has Y polarization, and the other (i.e., antenna 14) is positioned in the X direction and has X polarization. It is to be understood that the incident wave (corresponding with the stimulation frequency of the material 16 studied) may have either X, or Y, or a combined polarization, and that the local electromagnetic field at the gap G may not be greatly enhanced as a result of either of the antennas 12, 14. Rather, in this example, both types of Raman scattering (Stokes and anti-Stokes) are enhanced during the radiation process as a result of the respective antennas 12, 14. It is to be understood that the polarization of the respective Raman signals will correspond with the polarization of the antenna 12 or 14 configured for that particular signal's enhancement. For example, the Stokes signals will have Y polarization (corresponding with antenna 12) and the anti-Stokes signals will have X polarization (corresponding with antenna 14). In this particular example, since the polarization of each antenna 12, 14 is in a different direction, the enhanced signals are also advantageously radiated at different polarizations.

As shown in FIG. 2, any embodiment of the device 100 may be established on a substrate 18. It is to be understood that the antennas 12, 14 are configured so that they resonate in a desirable manner on the substrate 18. As such, the substrate 18 selected may be taken into consideration when determining the geometry of the antennas 12, 14 in order to achieve the desirable resonance of each antenna 12, 14. Non-limiting examples of suitable substrate materials include insulators (e.g., glass, quartz, ceramic, alumina, etc.), polymeric material(s) (e.g., polycarbonate, polyamide, acrylics, etc.), or semiconductors (e.g., silicon, InP, GaAs, InAs, $Ga_xAl_{1-x}As$ (where $0<x<1$), $In_xGa_{1-x}As_yP_{1-y}$ (where $0<x<1$, $0<y<1$)), silicon-on-insulator (SOI) substrates, or group III-V semiconductors established on silicon or SOI substrates. Still further, in one embodiment, the substrate 18 is not a facet of a laser.

Figure 3A:
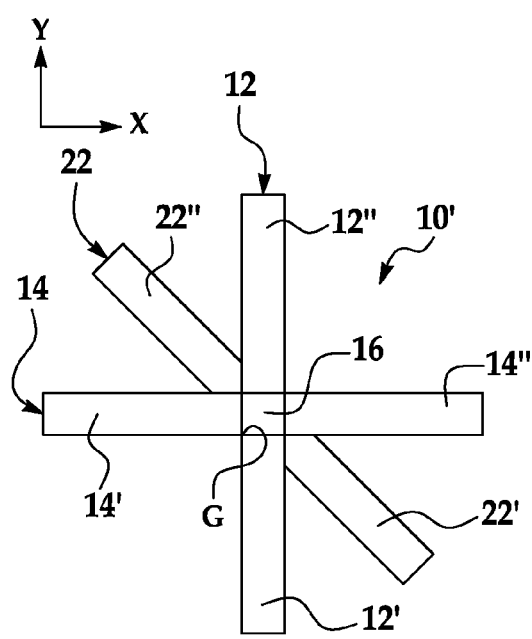
FIG. 3A is a top view of another embodiment, in accordance with the present disclosure, of a device for type selective and polarization selective Raman spectroscopy.
Figure 3B:
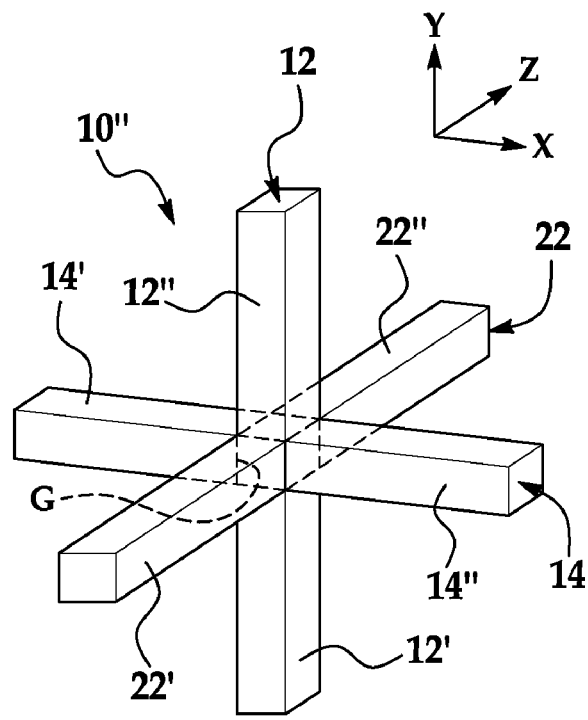
FIG. 3B is a perspective view of another embodiment, in accordance with the present disclosure, of a device including a single antenna set for type selective and polarization selective Raman spectroscopy.
Figure 3C:
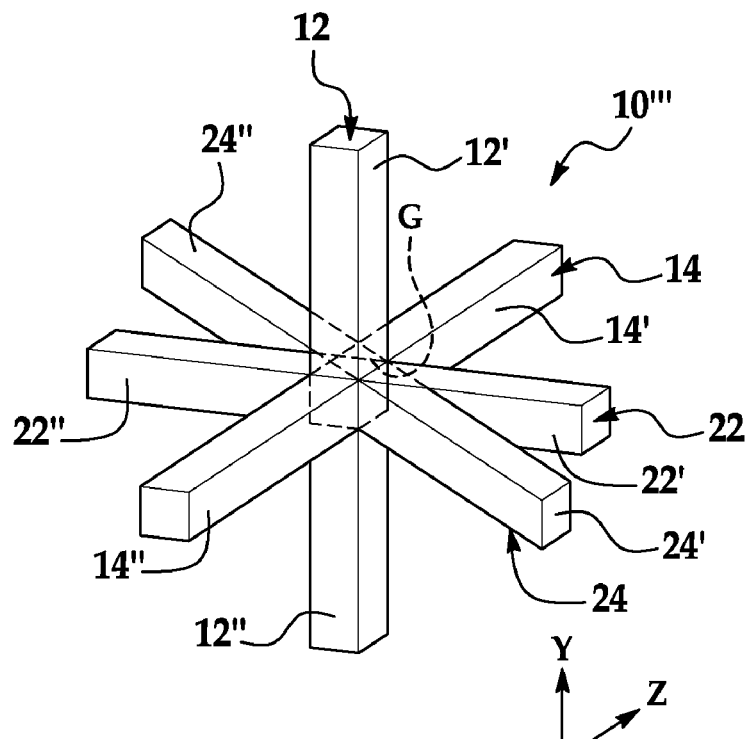
FIG. 3C is a perspective view of still another embodiment, in accordance with the present disclosure, of a device including a single antenna set for type selective and polarization selective Raman spectroscopy.

Referring now to FIGS. 3A, 3B, and 3C, other embodiments of the antenna set 10', 10", and 10''' are respectively depicted. In the embodiment shown in FIG. 3A, a third linear antenna 22 (including segments 22' and 22") crosses each of the first and second antennas 12, 14 at respective non-zero angles. In the embodiment shown in FIG. 3B, the third linear antenna 22 crosses each of the first and second antennas 12, 14 such that it is perpendicular to each of the other antennas 12, 14. In the embodiment shown in FIG. 3C, the third linear antenna 22 crosses each of the first and second antennas 12, 14 such that it is perpendicular to each of the other antennas 12, 14, and a fourth linear antenna 24 (including segments 24' and 24") is in the same plane as the third linear antenna 22 but crosses the antenna 22 at a non-zero angle. In each of these embodiments, the gap G and any material 16 established therein is shared by all of the antennas 12, 14, 22, 24. It is to be understood that the characteristics of the third and fourth antennas 22, 24 are designed in accordance with the selected material 16 so as to achieve the desirable polarization, and the desirable resonating frequency. The third and fourth antennas 22, 24 are generally configured at respective polarizations that are parallel to the direction of the particular antenna 22, 24, and to have a resonating frequency that is different than each of the other antennas 12, 14.

While the embodiments disclosed herein show two, three, and four crossing antennas 12, 14, 22, 24 in a set 10, 10', 10", 10''', it is to be understood that any desirable number of antennas 12, 14, 22, 24 may be included in the device 100. Potential limitations on the number of antennas 12, 14, 22, 24 that can be included in a device 100 include the size of the antennas 12, 14, 22, 24 and the space available around the gap G.

As a non-limiting example of the embodiment shown in FIG. 3A, the first antenna 12 may be configured to resonate at the stimulation frequency for Y polarization, the second antenna 14 may be configured to resonate at the selected material's corresponding Stokes frequency for X polarization, and the third antenna 22 may be configured to resonate at the selected material's corresponding anti-Stokes frequency for a polarization that is in the same plane as both the X and Y polarizations. In this embodiment, the polarization of the third antenna 22 is not entirely independent of, but is not the same as, the other two polarizations. The example given is for illustrative purposes, and it is to be understood that each of the antennas 12, 14, 22 may be configured at different resonating frequencies in order to enhance stimulation or scattering at those frequencies and at the respective polarizations, or two of the antennas 12 and 14, 14 and 22, or 12 and 22 may be configured to resonate at the same frequency in order to enhance stimulation or scattering at that particular frequency and at the respective polarizations.

In the non-limiting example shown in FIG. 3B, the first antenna 12 may be configured to resonate at the stimulation frequency for Y polarization, the second antenna 14 may be configured to resonate at the selected material's corresponding Stokes frequency for X polarization, and the third antenna 12 may be configured to resonate at the selected material's corresponding anti-Stokes frequency for Z polarization. The example given is for illustrative purposes, and it is to be understood that each of the antennas 12, 14, 22 may be configured at different resonating frequencies in order to enhance stimulation or scattering at those frequencies and at the respective polarizations, or two of the antennas 12 and 14, 14 and 22, or 12 and 22 may be configured to resonate at the same frequency in order to enhance stimulation or scattering at that particular frequency and at the respective polarizations.

In the non-limiting example shown in FIG. 3C, the first antenna 12 may be configured to resonate at the stimulation frequency for Y polarization, the second antenna 14 may be configured to resonate at the selected material's corresponding Stokes frequency for Z polarization, and the third and fourth antennas 22 and 24 may be configured to resonate at the selected material's corresponding anti-Stokes frequency respectively for Z polarization and for another polarization that is different than the polarization of each of antennas 12, 14 and 22. This example is also provided for illustrative purposes, and it is to be understood that at least two of the antennas 12 and 14, 14 and 22, 12 and 22, 12 and 24, or 14 and 24 may be configured at the same frequency in order to enhance stimulation at that particular frequency, while the other two of the antennas 22 and 24, 12 and 24, 14 and 24, 14 and 22, or 12 and 22 may be configured at the same frequency or at different frequencies in order to enhance scattering at that/those particular frequency/frequencies and polarization(s).

The antenna sets 10, 10', 10", 10''' disclosed herein are suitable for use in standard Raman detection procedures. A system 1000 for such a procedure is shown in FIG. 2 and includes the device 100 and a light source 20. In some embodiments, analyte molecules or particles are distributed in the previously empty gap G as the material 16 of interest, and are subsequently subjected to laser excitation of suitable material 16 stimulating wavelengths from the light source 20. In other embodiments, the material 16 filled in the gap G is of Raman interest and thus is studied using the device 100 including one or more of antenna sets 10, 10', 10", 10'''. The resulting signals are detected using known detector(s) (not shown).

Figure 4:
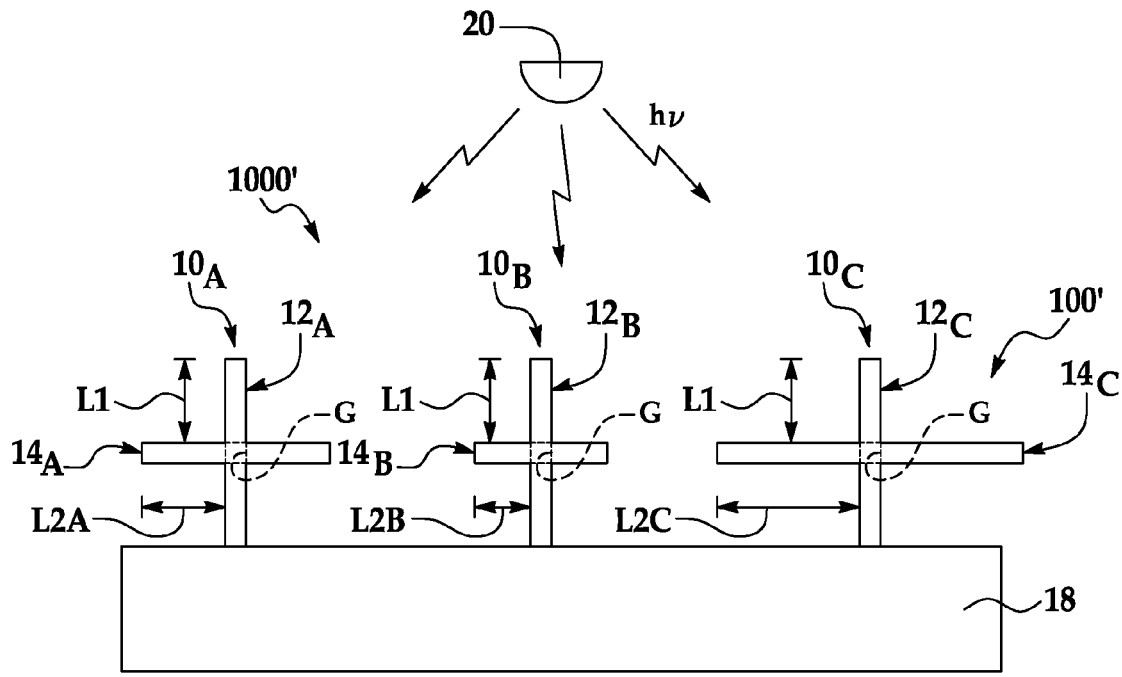
FIG. 4 is a schematic view of an embodiment, in accordance with the present disclosure, of a system and a device including multiple antenna sets for type selective and polarization selective Raman spectroscopy.
Figure 5:
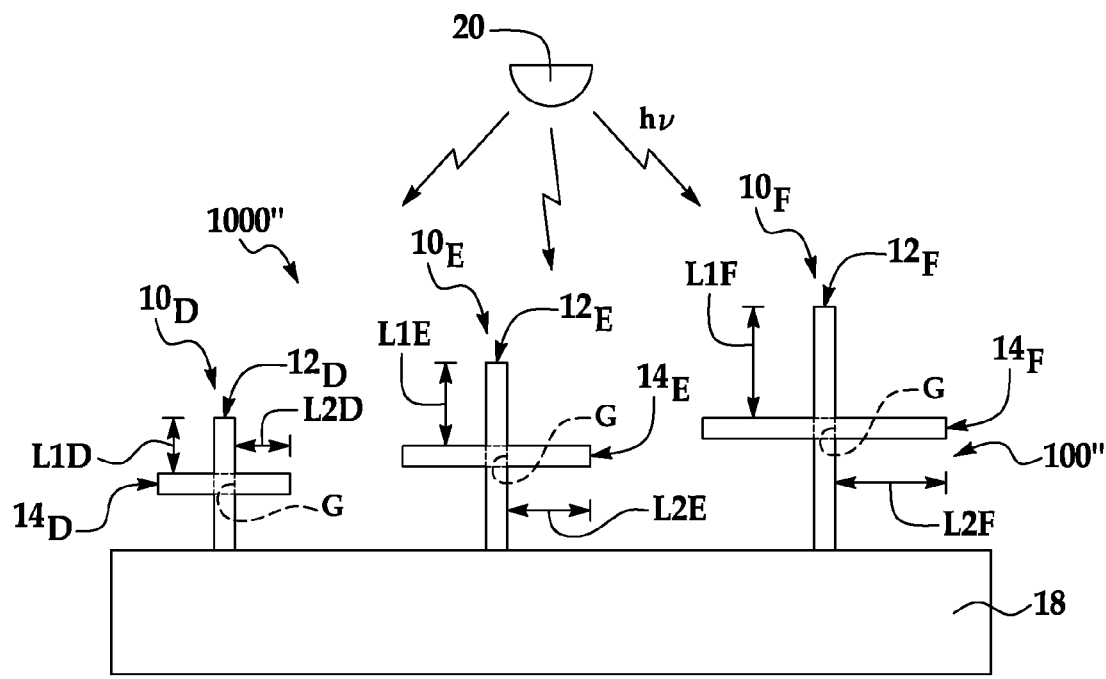
FIG. 5 is a schematic view of another embodiment, in accordance with the present disclosure, of a system and a device including multiple antenna sets for type selective and polarization selective Raman spectroscopy.

Other systems 1000', 1000" including other embodiments of the device 100', 100" are shown in FIGS. 4 and 5. In these embodiments, multiple antenna sets (shown as $10_A$, $10_B$, $10_C$ in FIG. 4 and $10_D$, $10_E$, $10_F$ in FIG. 5) are included in the device, for example, as an array on a substrate 18. The antenna sets $10_A$, $10_B$, $10_C$ and $10_D$, $10_E$, $10_F$ are established on any suitable substrate 18, such as those previously described, and are individually configured so that at least one of the antennas $14_A$, $14_B$, $14_C$ resonates at a different peak frequency for a material 16 of interest. While three sets ($10_A$, $10_B$, $10_C$ in FIG. 4 and $10_D$, $10_E$, $10_F$ in FIG. 5) are shown in the Figures, it is to be understood that any desirable number of antenna sets 10, 10', 10'', 10''', $10_A$, $10_B$, $10_C$, $10_D$, $10_E$, $10_F$ may be included in an array. In one embodiment, the number of sets 10, 10', 10'', 10''', $10_A$, $10_B$, $10_C$, $10_D$, $10_E$, $10_F$ included in an array will depend upon the number of different peak frequencies that are to be detected in the Raman spectrum and are characteristic of a material 16 of interest.

In the embodiment shown in FIG. 4, the first antennas $12_A$, $12_B$, $12_C$ of each antenna set $10_A$, $10_B$, $10_C$ have the same geometry (including the same half-length L1), and thus are configured at the same frequency, for example, to enhance stimulation. The second antennas $14_A$, $14_B$, $14_C$ of each antenna set $10_A$, $10_B$, $10_C$ have different geometries (including different half-lengths L2A, L2B, L2C, such that L2A≠L2B≠L2C). As such, each of the second antennas $14_A$, $14_B$, $14_C$ is configured to resonate at a different frequency, for example, to enhance scattering at those respective frequencies. For example, if a material 16 of interest to be introduced into the respective gaps G of the antenna sets $10_A$, $10_B$, $10_C$ has three different peaks of interest, one antenna $14_A$ of the first set $10_A$ may be configured to resonate at the Stokes or anti-Stokes frequency corresponding to the first peak of interest, one antenna $14_B$ of the second set $10_B$ may be configured to resonate at the Stokes or anti-Stokes frequency corresponding to the second peak of interest, and one antenna $14_C$ of the third set $10_C$ may be configured to resonate at the Stokes or anti-Stokes frequency corresponding to the third peak of interest. The individual responses of each of the antennas $14_A$, $14_B$, $14_C$ may be used together to identify the material 16. In this example, the other antenna $12_A$, $12_B$, $12_C$ in each set $10_A$, $10_B$, $10_C$ is designed to enhance the stimulation.

In the embodiment shown in FIG. 5, the first antennas $12_D$, $12_E$, $12_F$ of each antenna set $10_D$, $10_E$, $10_F$ have different geometries (including different half-lengths L1D, L1E, L1F, such that L1D≠L1E≠L1F), and thus are configured at different frequencies in order to enhance either Stokes or anti-Stokes scattering at a particular peak of interest of the material 16. The second antennas $14_D$, $14_E$, $14_F$ of each antenna set $10_D$, $10_E$, $10_F$ also have different geometries (including different half-lengths L2D, L2E, L2F, such that L2D≠L2E≠L2F), and thus are configured at different frequencies in order to enhance the other of anti-Stokes or Stokes scattering at the particular peak of interest of the material 16. For example, if a material 16 of interest to be introduced into the respective gaps G of the antenna sets $10_D$, $10_E$, $10_F$ has three different peaks of interest, one antenna $12_D$ of the first set $10_D$ may be configured to resonate at the Stokes frequency corresponding to the first peak of interest while the other antenna $14_D$ of the first set $10_D$ may be configured to resonate at the anti-Stokes frequency corresponding to the first peak of interest, and one antenna $12_E$ of the second set $10_E$ may be configured to resonate at the Stokes frequency corresponding to the second peak of interest while the other antenna $14_E$ of the second set $10_E$ may be configured to resonate at the anti-Stokes frequency corresponding to the second peak of interest, and one antenna $12_F$ of the third set $10_F$ may be configured to resonate at the Stokes frequency corresponding to the third peak of interest while the other antenna $14_F$ of the third set $10_F$ may be configured to resonate at the anti-Stokes frequency corresponding to the third peak of interest. The individual responses of each of the antenna sets $10_D$, $10_E$, $10_F$ may be used together to identify the material 16.

The embodiments of the antenna sets 10, 10', 10'', 10''' (as well as $10_A$, $10_B$, $10_C$, $10_D$, $10_E$, $10_F$) disclosed herein may be formed via any desirable technique. In one embodiment, the geometric pattern of the antennas 12, 14, and in some instances antennas 22, 24, the gap G, and the material 16 in the gap G are formed with the desirable dimensions and crossing at the desirable angle(s) θ by nanoimprint lithography, electron-beam lithography, photo-lithography, extreme ultraviolet (EUV) lithography, X-ray lithography, any other suitable lithography technique, or any other pattern defining technique. In another embodiment, the antennas 12, 14, and in some antennas 22, 24, the gap G, and the material 16 in the gap G are formed with the desirable dimensions and crossing at the desirable angle(s) θ by depositing desirable metal materials and the etching the metal materials to pattern the antennas 12, 14, and in some instances antennas 22, 24. In still another embodiment, the antennas 12, 14, and in some instances antennas 22, 24, are formed with the desirable dimensions and crossing at the desirable angle(s) θ by depositing the desirable metal materials and then using a lift-off technique to pattern the antennas 12, 14, and in some instances antennas 22, 24, from the deposited metal materials. In still another embodiment, the antennas 12, 14, and in some instances antennas 22, 24, the gap G, and the material 16 in the gap G are fabricated by direct deposition using focused ion beam. In yet another embodiment, the antennas 12, 14 (and in some instances antennas 22, 24), the gap G, and the material 16 in the gap G are fabricated by direct deposition using plating. The examples shown herein are illustrative and are by no means an exhaustive list.

Generating an embodiment of the device 10, 10', 10'', 10''' generally involves selecting a material 16 of interest, determining the desirable excitation frequency, and then configuring the geometry of the antennas 12, 14, 22, 24 to resonate at the desirable frequency and polarization. Designing the antennas 12, 14, 22, 24 disclosed herein is similar to designing antennas for use in the microwave region, which involves the use of established numerical/theoretical methods. However, when designing the antenna(s) 12, 14, 22, 24 disclosed herein, the appropriate optical properties are also considered.

To further illustrate embodiment(s) of the present disclosure, various examples are given herein. It is to be understood that these are provided for illustrative purposes and are not to be construed as limiting the scope of the disclosed embodiment(s).

EXAMPLE 1

The present inventors first numerically studied the resonating frequency of simulated single linear antennas. The results of this study indicated that the geometry of the antenna affects the resonating frequency. Three different linear antennas were simulated having similar linear shapes (i.e., a 20 nm width), as shown in FIG. 1A. The gap formed was 20 nm by 20 nm and was filled with silicon. The length for each antenna was different. The length of each segment of Antenna 1 was 113 nm long, the length of each segment of antenna 2 was 127 nm long, and the length of each segment of antenna 3 was 140 nm long. FIG. 1B illustrates the ratio of the square of the electric field magnitude at the center of each antenna gap to that of the incident wave as the frequency changes. The numerical study was performed using a finite element method (FEM) with a commercially available software package from COMSOL. As depicted in FIG. 1B, the frequency response changed greatly when the antenna length was changed.

EXAMPLE 2

The present inventors then numerically studied the effect that crossing two different linear antennas such that they share a common gap would have on the frequency response and polarization of the Raman scattering of the gap material (refer to FIG. 2). One antenna was configured to operate at the stimulating frequency of the material in the gap, and the other antenna was designed to operate at the anti-Stokes scattering frequency. It is to be understood that the second antenna could also have been designed to operate at the Stokes scattering frequency instead of the anti-Stokes scattering frequency.

More specifically, each simulated antenna was made of silver, and the width of each antenna was 20 nm. As such, the gap was 20 nm by 20 nm. The material inside the gap was silicon. The length of each segment of the first antenna was 140 nm, and as such, this antenna was configured to resonate around 1550 nm free space wavelength, which is the stimulating wavelength for silicon that would be used with an actual antenna for studying Raman scattering of silicon. The polarization of this antenna was along the X axis. The length of each segment of the second antenna was 110 nm, and as such, this antenna was configured to resonate around 1434 nm, which is the anti-Stokes frequency of silicon when 1550 nm excitation is used. The polarization of this antenna was along the Y axis.

Figure 6:
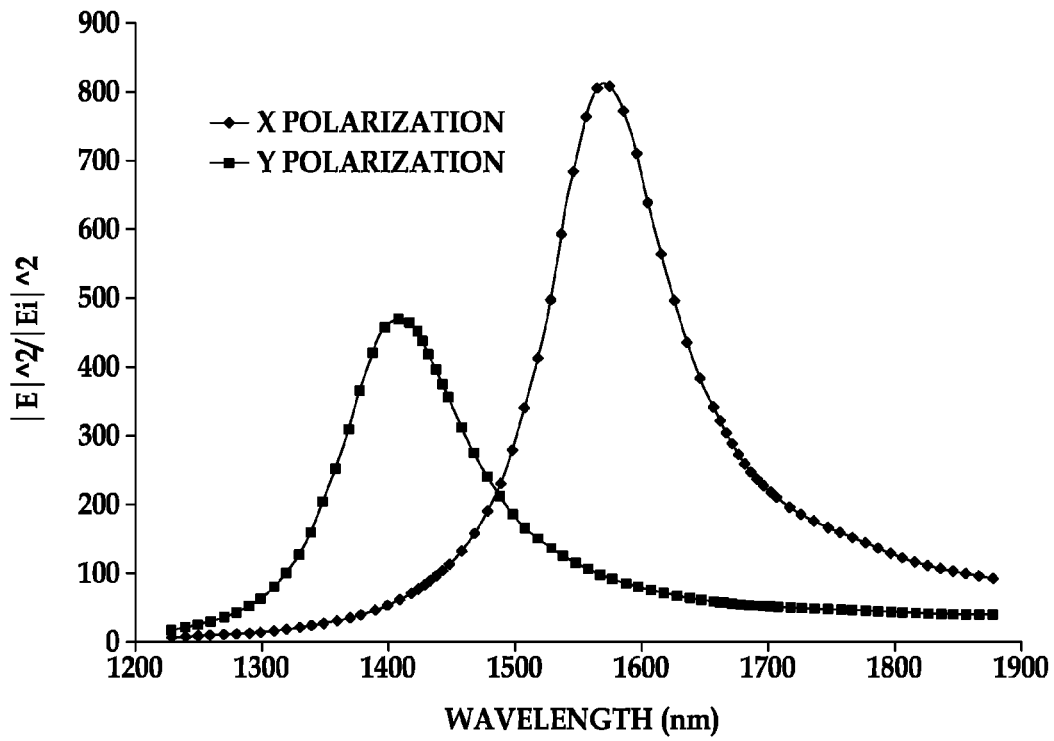
FIG. 6 is a graph illustrating, for an embodiment, in accordance with the present disclosure, of the device including intersecting antennas, the ratio of the square of the electric field magnitude at a shared center of the antennas to the square of the incident wave as a function of wavelength, for two different incident electromagnetic field polarizations indicated in the Figure.

FIG. 6 illustrates the ratio of the square of the electric field magnitude at the center of the device to that of the incident wave as the frequency changes, for each of the X and Y polarizations. From FIG. 6, it can be seen that the device has two resonances with different resonant frequencies when excited by incident EM waves with different polarizations. Each of the resonant frequencies corresponds to the resonant frequency of the individual antenna that is parallel to the excitation polarization. When the system is excited by an incidence of a 1550 nm free space wavelength that is polarized along the X direction, the local field at the gap was greatly enhanced, as shown via the diamond marked line in FIG. 6. The excitation process of the Raman scattering of the gap material (in this example, silicon) is then greatly enhanced. It is to be understood that both the Stokes (radiating at 1434 nm) and the anti-Stokes (radiating at 1434 nm) Raman scattering are possible. Since the second antenna in this simulated example resonates at 1434 nm (see the square marked line in FIG. 4), it can be concluded that the radiation of the anti-Stokes Raman scattering is greatly enhanced by this antenna, and that the device possesses a relatively dominant strength in the Raman scattering (i.e., the ratio of the anti-Stokes signal to the Stokes signal is much higher compared to the situation when such a device is not used).

Likewise, if the second antenna is designed to resonate at the Stokes frequency (1686 nm), the Stokes Raman scattering can be greatly enhanced, and the device will possess a relatively dominant strength in the Raman scattering.

The numerical study of Example 2 was also performed using a finite element method (FEM) with a commercially available software package from COMSOL.

EXAMPLE 3

The present inventors again numerically studied the effect that crossing two different, simulated linear antennas such that they share a common gap would have on the frequency response and polarization of the gap material (again refer to FIG. 2). In this example, one antenna was configured to operate at the Stokes scattering frequency of the material in the gap for a certain stimulation/excitation frequency (e.g., 1550 nm free space wavelength excitatino), and the other antenna was designed to operate at the anti-Stokes scattering frequency for the same stimulation/excitation frequency.

More specifically, each simulated antenna was made of silver, and the width of each antenna was 20 nm. As such, the gap was 20 nm*20 nm. The material inside the gap was silicon. The length of each segment of the first antenna was 164 nm, and as such, this antenna was configured to resonate around 1686 nm (i.e., the Stokes scattering in silicon for 1550 nm excitation). The polarization of this antenna was along the Y axis. The length of each segment of the second antenna was 115 nm, and as such, this antenna was configured to resonate around 1434 nm (i.e., the anti-Stokes scattering in silicon for 1550 nm excitation). The polarization of this antenna was along the X axis.

Figure 7:
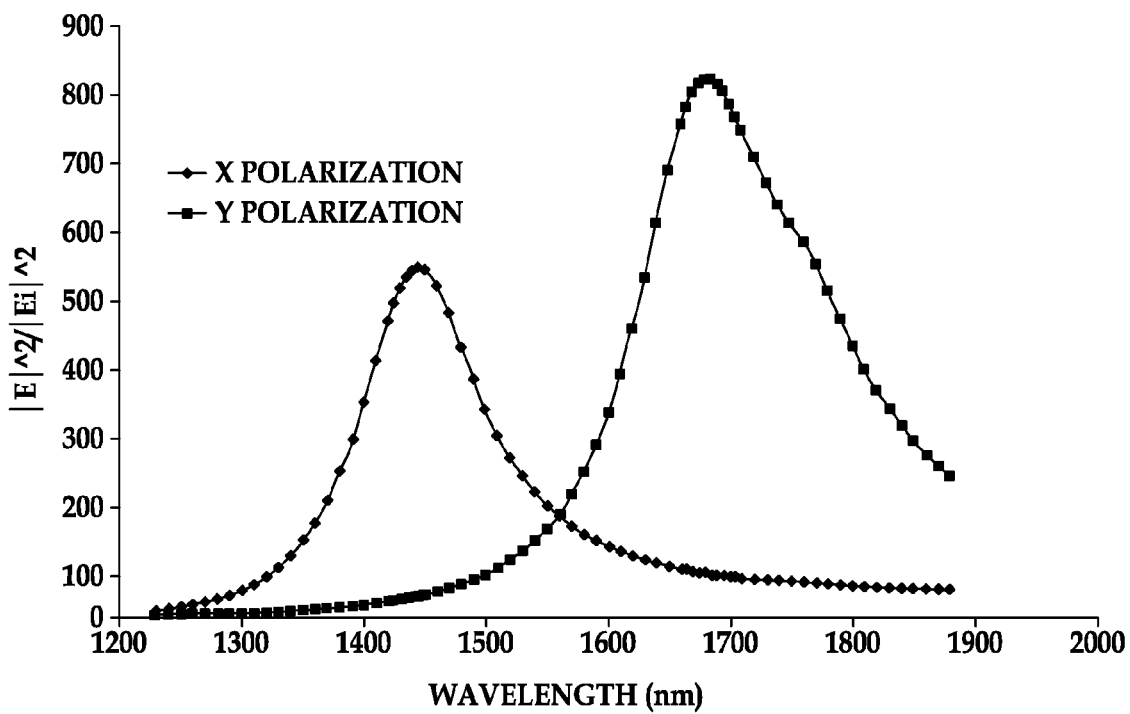
FIG. 7 is a graph illustrating, for another embodiment, in accordance with the present disclosure, of the device including intersecting antennas, the ratio of the square of the electric field magnitude at a shared center of the antennas to the square of the incident wave as a function of wavelength, for two different incident electromagnetic field polarizations indicated in the Figure.

FIG. 7 illustrates the ratio of the square of the electric field magnitude at the center of the device to that of the incident wave as the frequency changes, for each of the X and Y polarizations. From FIG. 7, it can be seen that the device has two resonances with different resonant frequencies when excited with different polarizations. Each of the resonant frequencies corresponds to the resonant frequency of the individual antenna that is parallel to the excitation polarization. When the system is excited by an incidence of a 1550 nm free space wavelength of arbitrary excitation, the local field at the stimulation frequency was not necessarily greatly enhanced (for example, as compared to the stimulation frequency enhancement of Example 2), and thus the excitation process of Raman scattering is not greatly enhanced. However, Raman scattering is still enhanced because the radiation process is assisted due to the two optical antennas. Both the Stokes and anti-Stokes and the anti-Stokes scattering were enhanced by a respective antenna. Furthermore, the two scatterings were distributed at perpendicular polarizations.

While several embodiments have been described in detail, it will be apparent to those skilled in the art that the disclosed embodiments may be modified. Therefore, the foregoing description is to be considered exemplary rather than limiting.

What is claimed is:

1. A type selective and polarization selective device for Raman spectroscopy, the device comprising:
   a set of at least two antennas, including:
      a first antenna having a first geometry such that the first antenna is configured to resonate, for one of a first polarization or a second polarization that is different from the first polarization, at one of a predetermined stimulation frequency of a material for which Raman scattering is to be studied, a Stokes frequency corresponding with the material when excited at the predetermined stimulation frequency, or an anti-Stokes frequency corresponding with the material when excited at the predetermined stimulation frequency; and
      a second antenna intersecting the first antenna, the second antenna having a second geometry such that the second antenna is configured to resonate, for an other of the second polarization or the first polarization, at the Stokes frequency when the first antenna is configured to resonate at the predetermined stimulation frequency or at the anti-Stokes frequency, or at the anti-Stokes frequency when the first antenna is configured to resonate at the predetermined stimulation frequency or at the Stokes frequency, or at the predetermined stimulation frequency when the first antenna is configured to resonate at the Stokes frequency or at the anti-Stokes frequency; and a gap located at an intersection of the at least two antennas, the gap configured to have the material established therein.

2. The device as defined in claim 1 wherein the first antenna geometry is different from the second antenna geometry.

3. The device as defined in claim 1, further comprising a third antenna intersecting both the first and second antennas, the third antenna having a third geometry such that the third antenna is configured to resonate, for a polarization other than the first polarization or the second polarization, at the Stokes frequency when the first antenna is configured to resonate at the predetermined stimulation frequency or at the anti-Stokes frequency, or at the anti-Stokes frequency when the first antenna is configured to resonate at the predetermined stimulation frequency or at the Stokes frequency, or at the predetermined stimulation frequency when the first antenna is configured to resonate at the Stokes frequency or at the anti-Stokes frequency.

4. The device as defined in claim 1, further comprising the material established in the gap, wherein the material is selected from chemical species, biological species, and combinations thereof.

5. The device as defined in claim 4 wherein the material established in the gap is silicon, wherein the antenna set is established on a silicon dioxide substrate, and wherein a length of each segment of the first antenna is 140 nm and the first antenna is configured to resonate at a stimulation frequency of silicon for X polarization, and wherein a length of each segment of the second antenna is 110 nm and the second antenna is configured to resonate at an anti-Stokes frequency of silicon for Y polarization.

6. The device as defined in claim 4 wherein the material established in the gap is silicon, wherein the antenna set is established on a silicon dioxide substrate, and wherein a length of each segment of the first antenna is 164 nm and the first antenna is configured to resonate at a Stokes frequency of silicon for Y polarization, and wherein a length of each segment of the second antenna is 115 nm and the second antenna is configured to resonate at an anti-Stokes frequency of silicon for X polarization.

7. The device as defined in claim 1 wherein the first antenna is configured to enhance a local field at the predetermined stimulation frequency which in turn enhances an excitation process of the Raman scattering, and wherein a radiation process at the Stokes frequency is enhanced by the second antenna that is configured to resonate at the Stokes frequency.

8. The device as defined in claim 1 wherein the first antenna is configured to enhance a local field at the predetermined stimulation frequency which in turn enhances an excitation process of the Raman scattering, and wherein a radiation process at the anti-Stokes frequency is enhanced by the second antenna that is configured to resonate at the anti-Stokes frequency.

9. The device as defined in claim 1 wherein each of the first and second antennas is linear.

10. The device as defined in claim 1, further comprising:
a substrate upon which the set is established; and
at least one other set of at least two other antennas established on the substrate, the at least one other set including:
an other first antenna having an other first geometry such that the other first antenna is configured to resonate, for one of a first polarization or a second polarization that is different from the first polarization, at one of the predetermined stimulation frequency of the material, a Stokes frequency corresponding with a peak of the material when excited at the predetermined stimulation frequency, or an anti-Stokes frequency corresponding with a peak of the material when excited at the predetermined stimulation frequency, wherein when the other first antenna is configured to resonate at the Stokes or anti-Stokes frequency for the peak of the material, the peak is different from a peak of the material at which the first antenna of the set is configured to resonate; and
an other second antenna intersecting the other first antenna, the other second antenna having an other second geometry such that the other second antenna is configured to resonate, for an other of the second polarization or the first polarization, at the Stokes frequency when the other first antenna is configured to resonate at the predetermined stimulation frequency or at the anti-Stokes frequency, or at the anti-Stokes frequency when the other first antenna is configured to resonate at the predetermined stimulation frequency or at the Stokes frequency, or at the predetermined stimulation frequency when the other first antenna is configured to resonate at the Stokes frequency or at the anti-Stokes frequency, wherein when the other second antenna is configured to resonate at the Stokes or anti-Stokes frequency for the peak of the material, the peak is different from a peak of the material at which the second antenna of the set is configured to resonate; and
a gap located at an intersection of the at least two other antennas, the gap configured to have the material established therein.

11. A type selective and polarization selective system for Raman spectroscopy, comprising:
a light source; and
a Raman scattering device configured to have light from the light source incident thereon, the Raman scattering device including:
a set of at least two antennas, including:
a first antenna having a first geometry such that the first antenna is configured to resonate, for one of a first polarization or a second polarization that is different from the first polarization, at one of a predetermined stimulation frequency of a material for which Raman scattering is to be studied, a Stokes frequency corresponding with the material when excited at the predetermined stimulation frequency, or an anti-Stokes frequency corresponding with the material when excited at the predetermined stimulation frequency; and
a second antenna intersecting the first antenna, the second antenna having a second geometry such that the second antenna is configured to resonate, for an other of the second polarization or the first polarization, at the Stokes frequency when the first antenna is configured to resonate at the predetermined stimulation frequency or at the anti-Stokes frequency, or at the anti-Stokes frequency when the first antenna is configured to resonate at the predetermined stimulation frequency or at the Stokes frequency, or at the predetermined stimulation frequency when the first antenna is configured to resonate at the Stokes frequency or at the anti-Stokes frequency; and
a gap located at an intersection of the first and second antennas, the gap configured to have the material established therein.

12. The system as defined in claim 11 wherein the light source is configured to emit the predetermined stimulation frequency, and wherein the system further comprises a detector configured to detect at least one of the Stokes frequency or the anti-Stokes frequency.

13. A method for making a type selective and polarization selective device for Raman spectroscopy, the method comprising:
selecting a geometry for a first of at least two antennas such that the first antenna resonates, for a first polarization, at one of a predetermined stimulation frequency of a material for which Raman scattering is to be studied, a Stokes frequency corresponding with the material when excited at the predetermined stimulation frequency, or an anti-Stokes frequency corresponding with the material when excited at the predetermined stimulation frequency;
selecting a geometry for a second of the at least two antennas such that the second antenna resonates, for a second polarization that is different from the first polarization, at the Stokes frequency when the first antenna is configured to resonate at the predetermined stimulation frequency or at the anti-Stokes frequency, or at the anti-Stokes frequency when the first antenna is configured to resonate at the predetermined stimulation frequency or at the Stokes frequency, or at the predetermined stimulation frequency when the first antenna is configured to resonate at the Stokes frequency or at the anti-Stokes frequency; and
establishing the at least two antennas such that the first and second antennas intersect at a shared gap, the shared gap configured to have the material established therein.

14. The method as defined in claim 13 wherein establishing the at least two antennas includes positioning the first antenna 90° with respect to the second antenna such that the first and second antennas exhibit perpendicular polarizations.

15. The method as defined in claim 13, further comprising enhancing Stokes scattering by:
selecting a length for each segment of the first antenna such that the first antenna enhances a local field at the predetermined stimulation frequency, thereby enhancing an excitation process of the Raman scattering; and
selecting a length for each segment of the second antenna such that the second antenna resonates at the Stokes frequency, thereby enhancing a radiation process at the Stokes frequency.

16. The method as defined in claim 13, further comprising enhancing anti-Stokes scattering by:
selecting a length for each segment of the first antenna such that the first antenna enhances a local field at the predetermined stimulation frequency, thereby enhancing an excitation process of the Raman scattering; and
selecting a length for each segment of the second antenna such that the second antenna resonates at the anti-Stokes frequency, thereby enhancing a radiation process at the anti-Stokes frequency.

17. The method as defined in claim 13, further comprising enhancing both Stokes and anti-Stokes scattering by:
selecting a length for each segment of the first antenna such that the first antenna resonates at the Stokes frequency, thereby enhancing a radiation process at the Stokes frequency; and
selecting a length for each segment of the second antenna such that the second antenna resonates at the anti-Stokes frequency, thereby enhancing a radiation process at the anti-Stokes frequency.

18. The method as defined in claim 13 wherein establishing the first and second antennas is accomplished by i) at least one of nanoimprint lithography, electron-beam lithography, photo-lithography, extreme ultraviolet (EUV) lithography, or X-ray lithography; or ii) deposition and etching of a metal material; or iii) deposition of a metal material and lift-off to pattern the metal material.

19. The method as defined in claim 13, further comprising:
selecting a geometry for a third of the at least two antennas such that the third antenna is configured to resonate, for a third polarization other than the first polarization or the second polarization, at the Stokes frequency when the first antenna is configured to resonate at the predetermined stimulation frequency or at the anti-Stokes frequency, or at the anti-Stokes frequency when the first antenna is configured to resonate at the predetermined stimulation frequency or at the Stokes frequency, or at the predetermined stimulation frequency when the first antenna is configured to resonate at the Stokes frequency or at the anti-Stokes frequency; and
establishing the third antenna such that the first, second and third antennas intersect at the shared gap.

20. The method as defined in claim 13 wherein prior to selecting the geometries of the first and second antennas, the method further comprises:
selecting a size of the gap;
selecting the material to be established in the gap; and
selecting the geometries of the first and second antennas to correspond with the selected gap size and material, thereby controlling the resonances of each of the first and second antennas.

* * * * *